(12) United States Patent
Gauthier et al.

(10) Patent No.: US 9,050,062 B1
(45) Date of Patent: Jun. 9, 2015

(54) MODULAR HANDLE CONSTRUCTION

(71) Applicants: Michael T. Gauthier, Grafton, WI (US); Robert F. Miller, Grafton, WI (US)

(72) Inventors: Michael T. Gauthier, Grafton, WI (US); Robert F. Miller, Grafton, WI (US)

(73) Assignee: Gauthier Biomedical, Inc., Grafton, WI (US)

(*) Notice: Subject to any disclaimer, the term of this patent is extended or adjusted under 35 U.S.C. 154(b) by 0 days.

(21) Appl. No.: 13/709,952

(22) Filed: Dec. 10, 2012

Related U.S. Application Data

(60) Provisional application No. 61/568,231, filed on Dec. 8, 2011.

(51) Int. Cl.
| | |
|---|---|
| *B25G 1/10* | (2006.01) |
| *A61B 19/00* | (2006.01) |
| *B29D 23/00* | (2006.01) |

(52) U.S. Cl.
CPC ............... *A61B 19/00* (2013.01); *B29D 23/00* (2013.01)

(58) Field of Classification Search
USPC ........ 16/431, 430; 81/177.1, 177.6, 489, 900; 173/210–212, 162.1, 162.2, 170
See application file for complete search history.

(56) References Cited

U.S. PATENT DOCUMENTS

| | | | | |
|---|---|---|---|---|
| 2,782,454 | A * | 2/1957 | Baer ................. | 16/431 |
| 4,826,168 | A * | 5/1989 | McGuire et al. ............. | 473/295 |
| 5,170,532 | A * | 12/1992 | Holmin et al. ................. | 16/431 |
| 5,680,800 | A * | 10/1997 | Sharpe ......................... | 81/177.2 |
| 5,713,104 | A * | 2/1998 | Giampaolo, Jr. ............... | 16/422 |
| 5,740,586 | A * | 4/1998 | Gomas ............................ | 16/436 |
| 5,911,798 | A * | 6/1999 | Arnold ........................ | 81/177.2 |
| 6,367,125 | B1 * | 4/2002 | Lin ................................ | 16/436 |
| 6,817,458 | B1 | 11/2004 | Gauthier | |
| 6,832,413 | B1 * | 12/2004 | Applewhite et al. ............ | 16/430 |
| 7,246,414 | B2 * | 7/2007 | Wu ................................ | 16/430 |
| 7,430,945 | B2 | 10/2008 | Gauthier et al. | |
| 7,441,310 | B2 * | 10/2008 | Chen .............................. | 16/430 |
| 7,877,843 | B2 * | 2/2011 | Holland-Letz ................... | 16/436 |
| 2004/0205938 | A1 * | 10/2004 | Blauer et al. ................. | 16/431 |
| 2005/0155186 | A1 * | 7/2005 | McGuyer et al. .............. | 16/430 |
| 2006/0169308 | A1 * | 8/2006 | Yen et al. ..................... | 135/25.4 |
| 2006/0174450 | A1 * | 8/2006 | Chen ............................. | 16/436 |
| 2006/0219419 | A1 * | 10/2006 | Sugiyama et al. ......... | 173/162.2 |
| 2007/0143966 | A1 * | 6/2007 | Fischer ............................ | 16/422 |
| 2007/0261208 | A1 * | 11/2007 | Ishai ............................... | 16/436 |
| 2010/0294084 | A1 | 11/2010 | Gauthier | |

* cited by examiner

*Primary Examiner* — Chuck Mah
(74) *Attorney, Agent, or Firm* — Boyle Fredrickson, S.C.

(57) ABSTRACT

A handle for a tool is provided that is formed of a core positioned within a sleeve of a temperature resistant material to form a handle with a space between the core and the sleeve. The core can be formed by machining a metal material while the sleeve and an optional skin positioned on the sleeve can be molded. The materials forming the sleeve and skin, and the space formed between the core and sleeve, create a handle that can be adapted to form a variety of different tools with different mechanisms located in the core that also has improved heat transfer characteristics for sterilization purposes.

12 Claims, 9 Drawing Sheets

MODULAR HANDLE CONSTRUCTION

CROSS-REFERENCE TO RELATED APPLICATION

This application claims priority from U.S. Provisional Application Ser. No. 61/568,231 filed on Dec. 8, 2011, the entirety of which is expressly incorporated herein by reference.

FIELD OF THE INVENTION

The present invention relates generally to handles for tools and more specifically to handles for medical devices that are subjected to harsh environments, such as handles which are periodically placed within an autocloave for sterilization purposes.

BACKGROUND OF THE INVENTION

There are many types of handles for tools of different types. These handles cam include within them various devices and mechanisms that enable the handle to perform various functions for the tools formed with the handle.

Many of these types of handles are used in situations that require that the handle be able to withstand very harsh environments during use of the tool or during cleaning of the tool. One example of handles of this type is a handle for a medical tool that must be sterilized by placing the handle in an autoclave. In the autoclave the handle is subjected to high temperature steam that effectively sterilizes the surfaces of the handle on which bacteria and other undesirable organisms may be located.

With prior art handles, the handle is normally formed with a central core formed of a single piece of a suitable material, such as a rigid metal. The metal core is machined and shaped as necessary to provide the desired structure for the various internal configuration or components for the tool to be positioned within the core. The shaping of the tool often requires that the core be intricately cut in a number of different sequential steps in order to achieve the desired shape to accommodate the particular configuration or shape of the components to be positioned within the core, which can greatly increase the costs and time required for creating the handle core.

Further, once machined into the desired configuration, the core of the tool is often formed with a molded material disposed around the exterior of the central core in order to provide the desired grip and aesthetic or appearance characteristics to the handle. To provide these characteristics to the handle, the molded material is formed in varying thicknesses on the exterior of the core. In most constructions, the molded layer is formed from an insulating type material, such as a silicone, which provides a desirable feel to the tool, while also being able to be formed with the desired shape around the core.

However, in those situations where the tool is required to be sterilized such as in an autoclave, the placement of the molded material directly around the exterior of the core can inhibit the transmission of heat from the exposed ends of the core to the interior of the core as a result of the insulating properties of the molded material. As a result, certain areas of the core may not be reached by the steam in order to achieve the necessary temperature for effective sterilization of the entire handle which can prevent the handle from being able to be used for its intended purpose.

Thus, it is desirable to develop a handle that can be formed with an outer molded layer of a suitable material that provides the desired characteristics to the handle while also enabling effective heat transfer to the entire core in order to quickly and effectively sterilize the core and the entire handle.

SUMMARY OF THE INVENTION

Briefly described, one aspect of the present disclosure provides a handle having a central core formed of a heat conducting material within which can be positioned any number of various types of mechanisms suitable for providing the desired utility for the tool. The core is positioned within a moldable sleeve of a relatively thin walled heat tolerant material having a relatively constant thickness. The sleeve includes interior features that enable the central core to be effectively positioned within and mated to the sleeve in the correct position. The sleeve also includes exterior features, and/or an exterior shape that enables an outer skin formed of the moldable, insulating material, such as silicone, placed on the exterior of the sleeve to have a relatively constant thickness across the entire length of the sleeve. In the assembled configuration, the core is held within the sleeve by an end cap engaged with the core and extending over the sleeve and the exterior of the skin.

In this configuration, the core and sleeve define an air space between the core and the sleeve that enables more effective heat transfer along the entire length of the core. This insulating effect of the skin on the core is consequently reduced as a result of the presence of the space and the more consistent thickness of the skin on the exterior of the sleeve. As a result, when the handle is disposed in an autoclave for the purposes of sterilizing the handle, the steam can more quickly raise the temperature of the core to enable the handle to be effectively heated and sterilized within the predetermined treatment cycles of the autoclave, even a high speed autoclave.

According to another aspect of the present disclosure, the core is formed with engagement surfaces for connecting and mating with sleeves having complementary surfaces, but the sleeves can be formed with any desired shape between the complementary surfaces. As a result, the same core configuration can be used with sleeves of various shapes.

According to still another aspect of the present disclosure, because the core is formed with a relatively simple and consistent configuration, regardless of the configuration of the remainder of the handle, the core can be formed with a variety of mechanisms for providing the desired utility for the handle.

Numerous other aspects, features, and advantages of the present invention will be made apparent from the following detailed description together with the drawings figures.

BRIEF DESCRIPTION OF THE DRAWINGS

The drawings illustrate the best mode currently contemplated of practicing the present invention.

In the drawings.

DETAILED DESCRIPTION OF THE INVENTION

Figure 1:
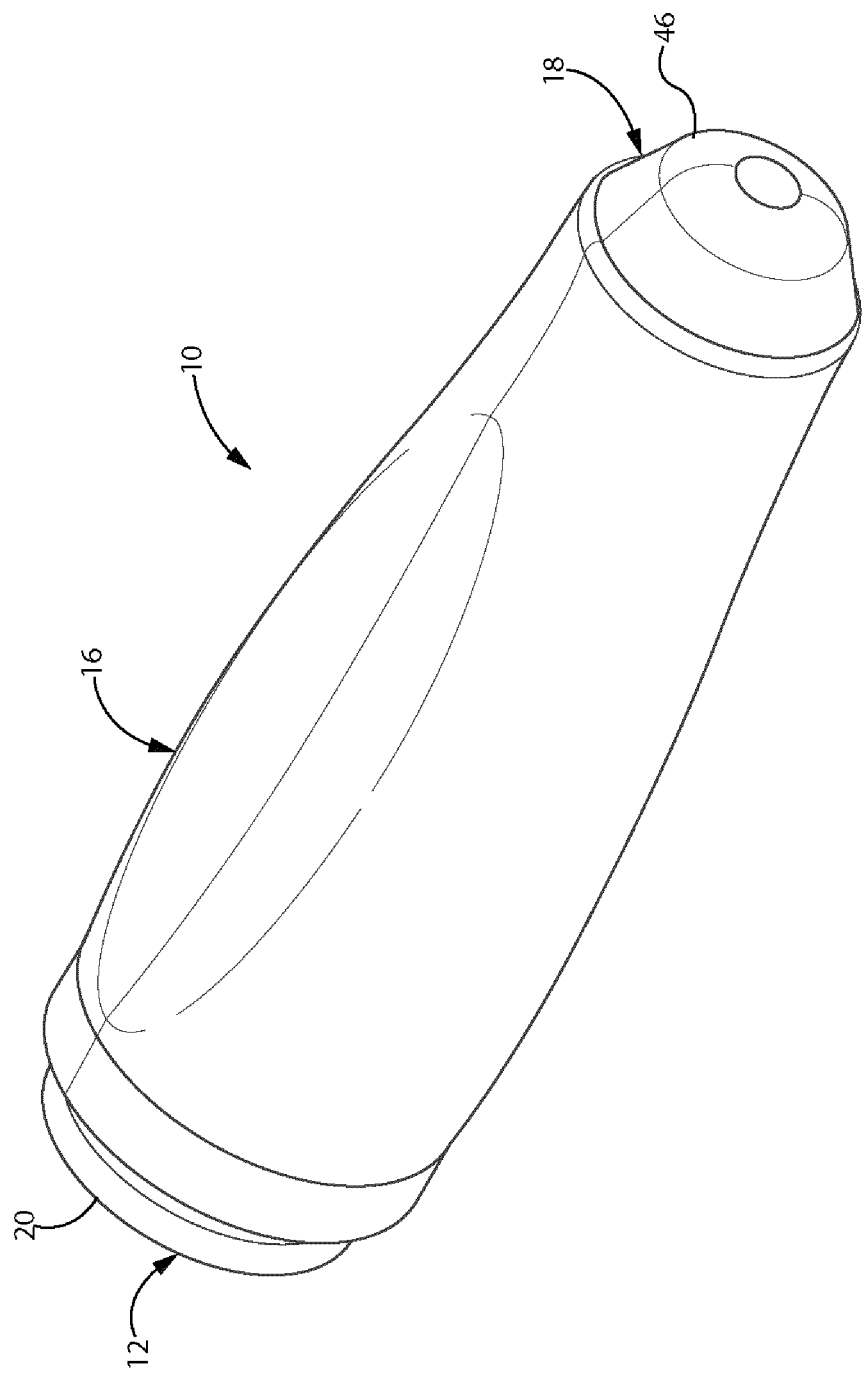
FIG. 1 is an isometric view of a one embodiment of a handle constructed according to the present disclosure.
Figure 2:
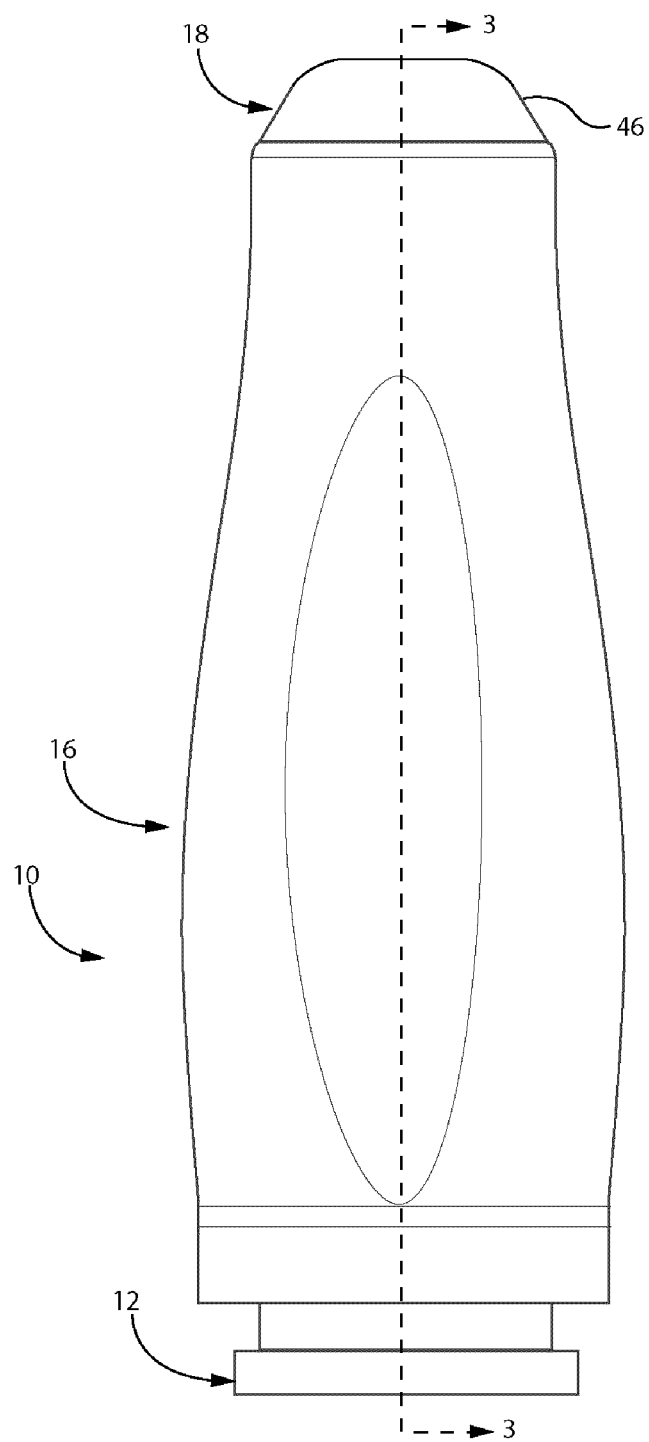
FIG. 2 is a side isometric view of the handle of FIG. 1.
Figure 3:
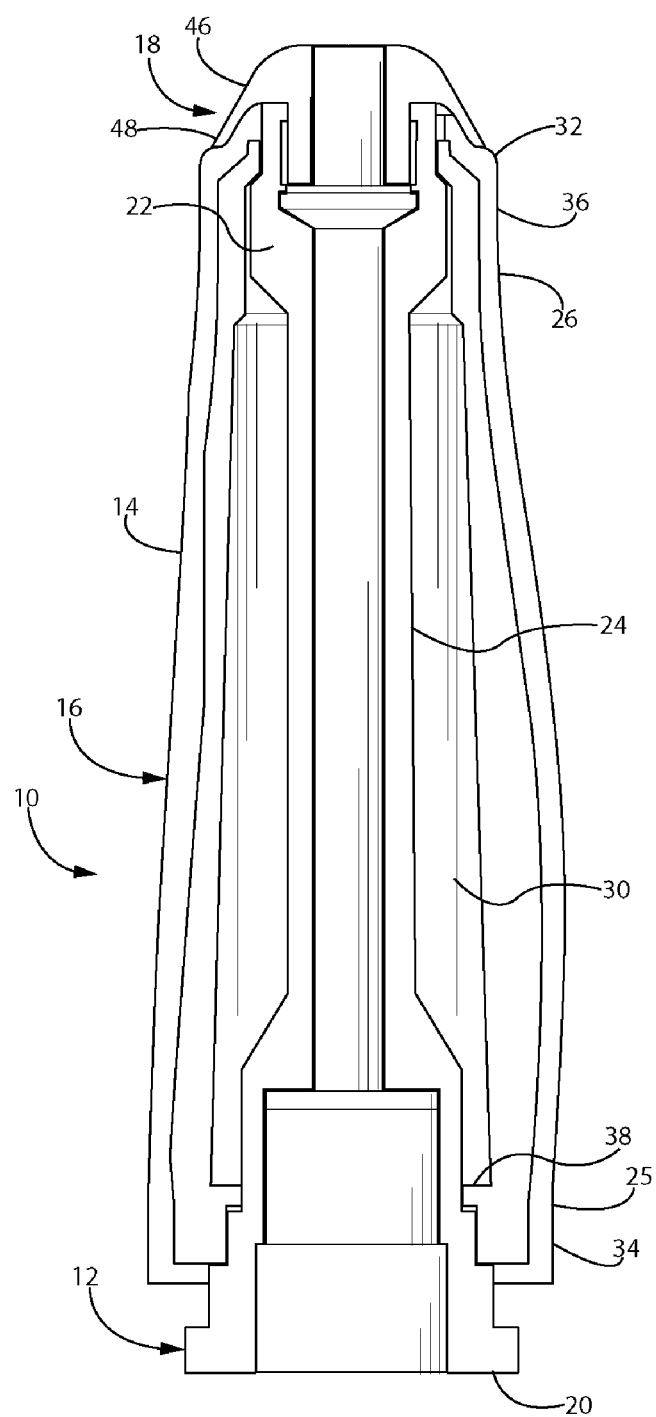
FIG. 3 is a cross-sectional view along line 3-3 of FIG. 2.
Figure 4:
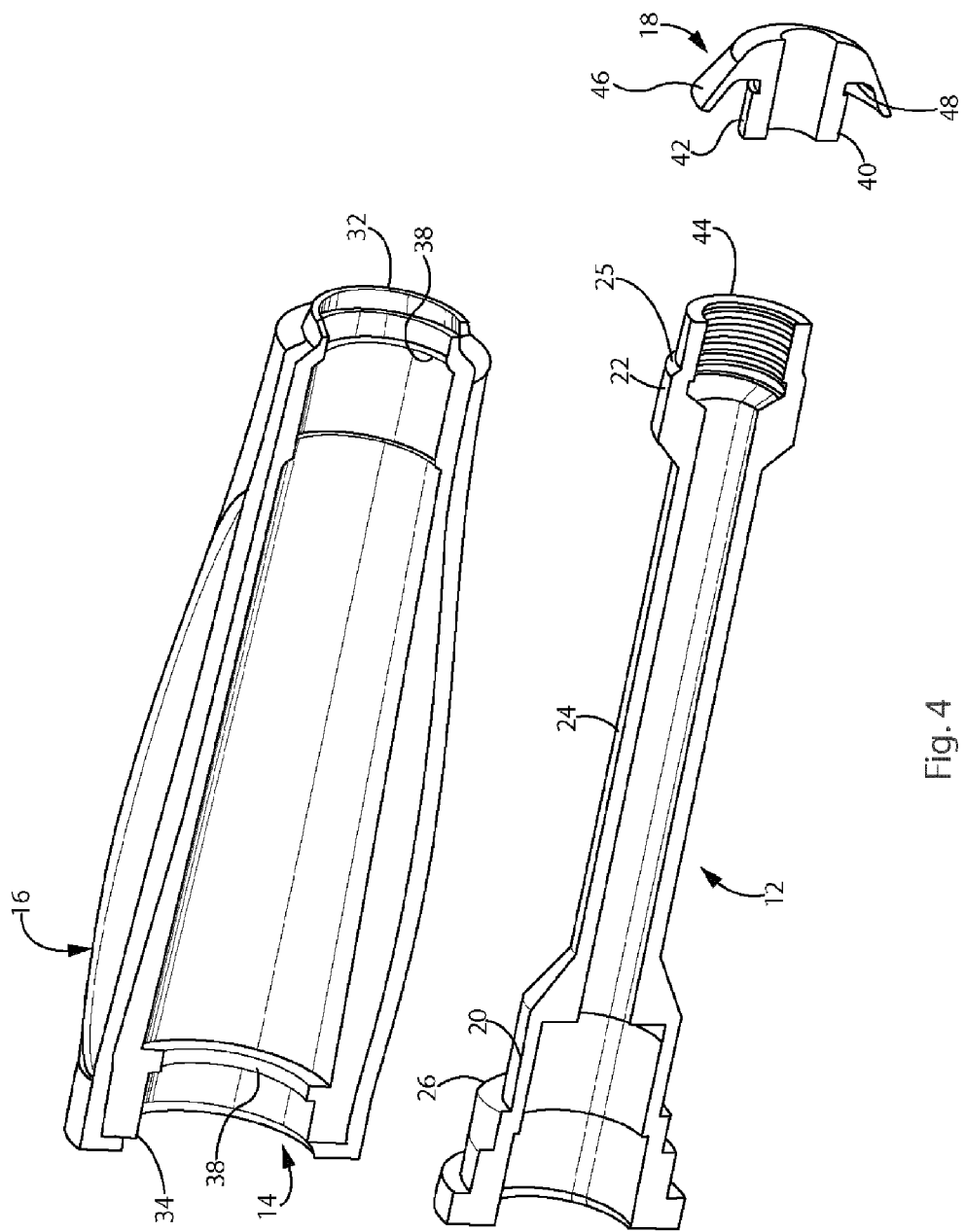
FIG. 4 is a partially exploded, cross-section isometric view of the handle of FIG. 3.
Figure 5:
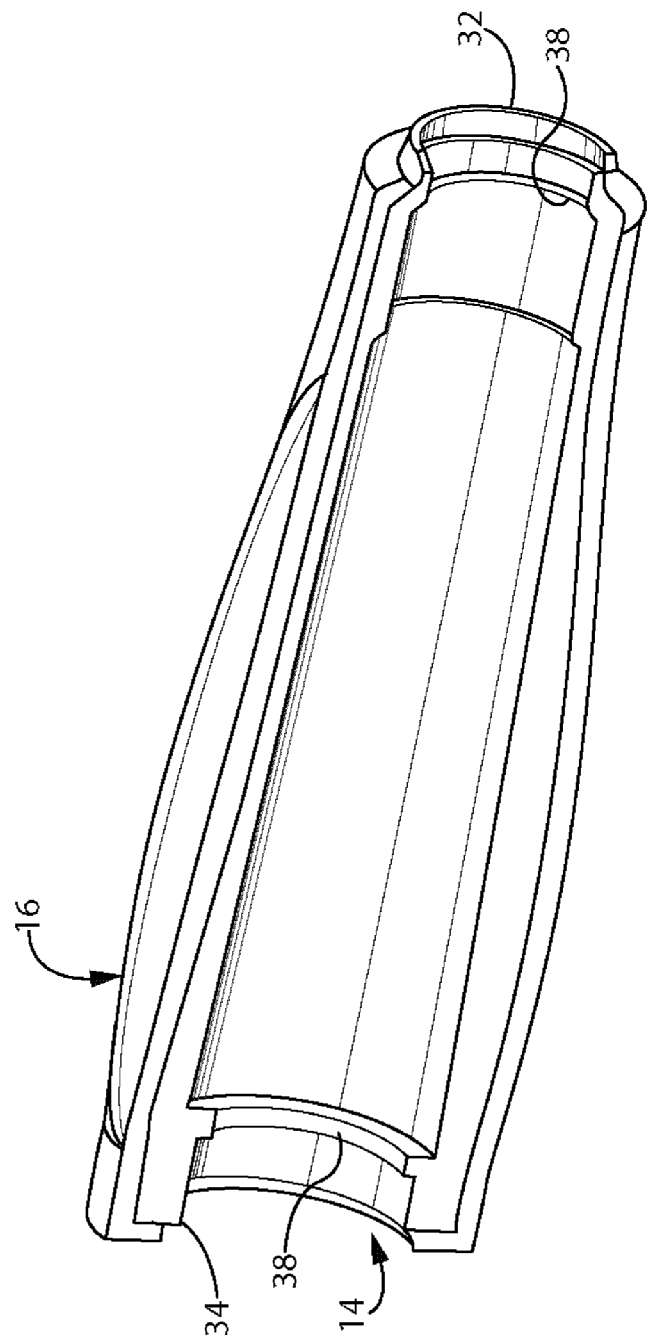
FIG. 5 is an isometric, cross-sectional view of the sleeve and skin of the handle of FIG. 4.
Figure 6:
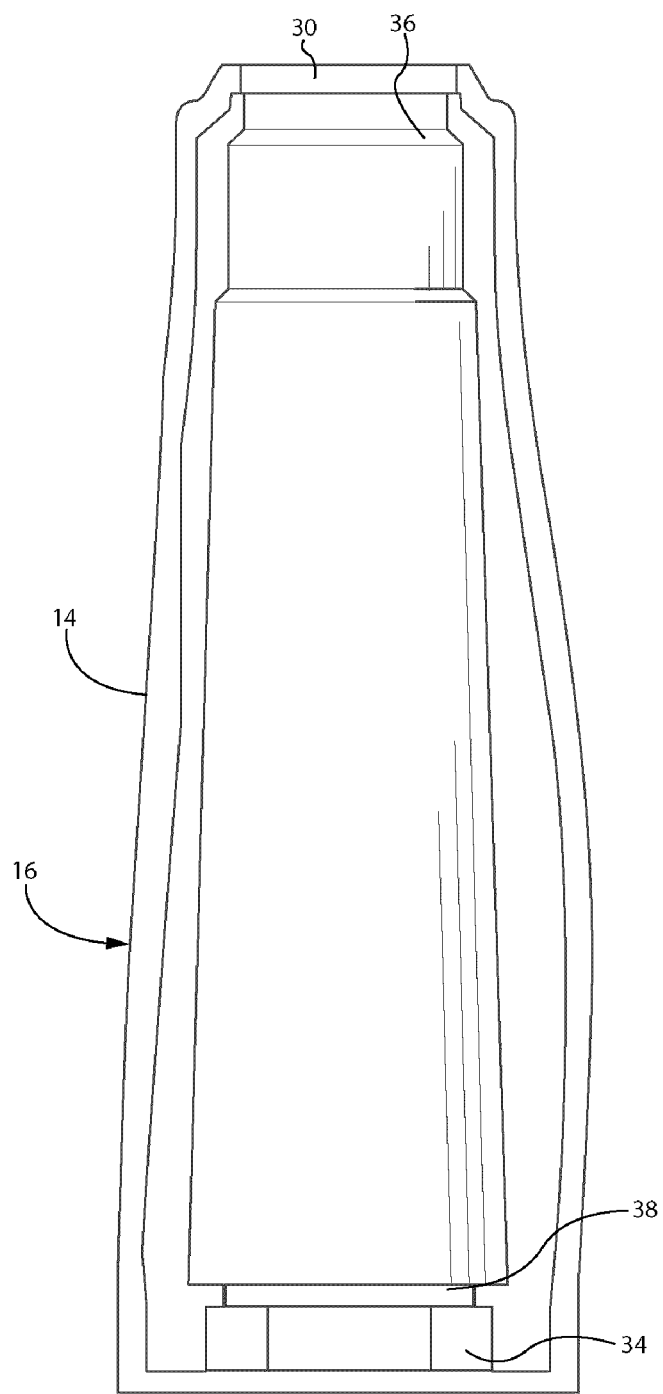
FIG. 6 is a side plan, cross-sectional view of the sleeve and skin of FIG. 5.
Figure 7:
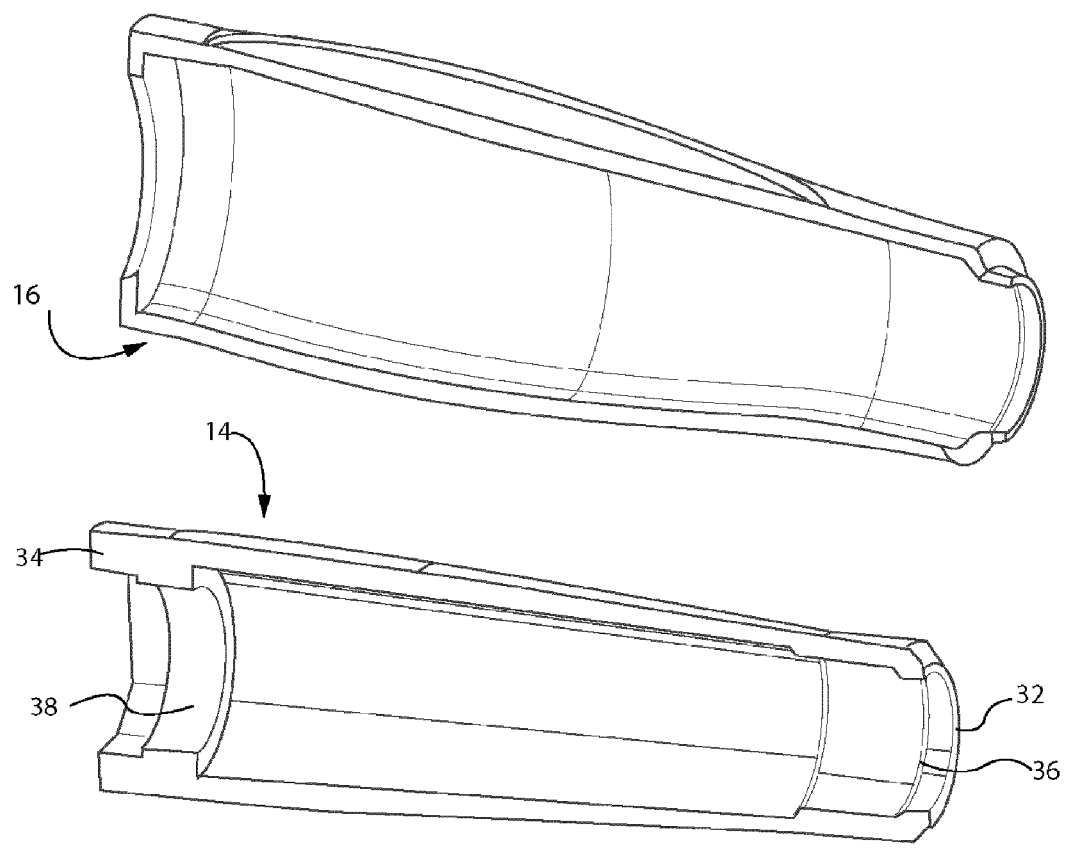
FIG. 7 is an exploded, isometric cross-sectional view of the sleeve and skin of FIG. 6.
Figure 8:
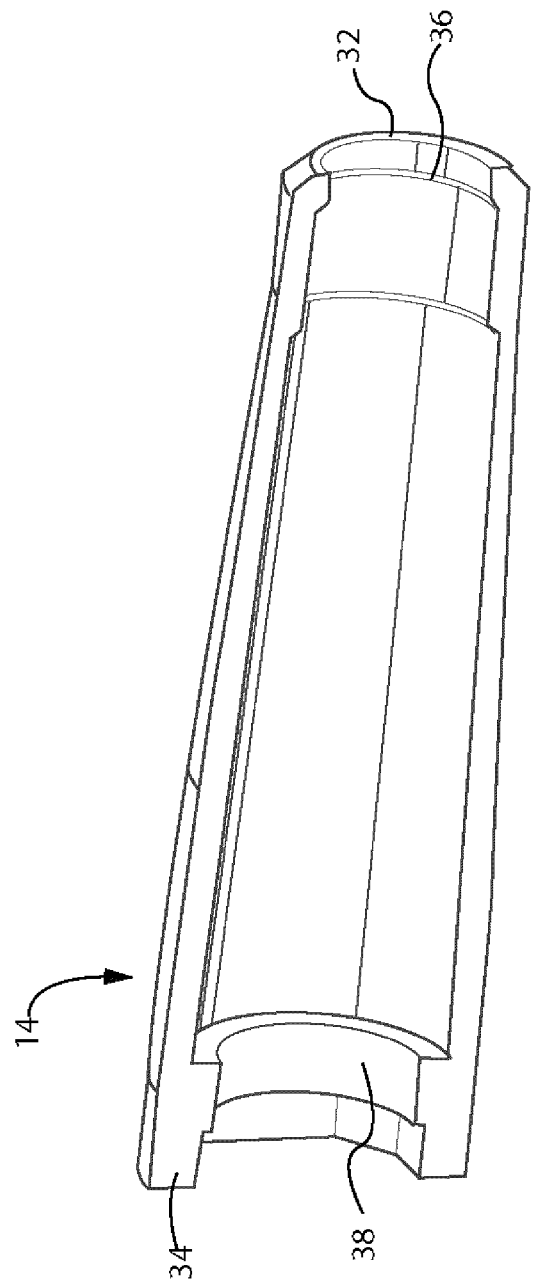
FIG. 8 is an isometric, cross-sectional view of the sleeve of FIG. 5.
Figure 9:
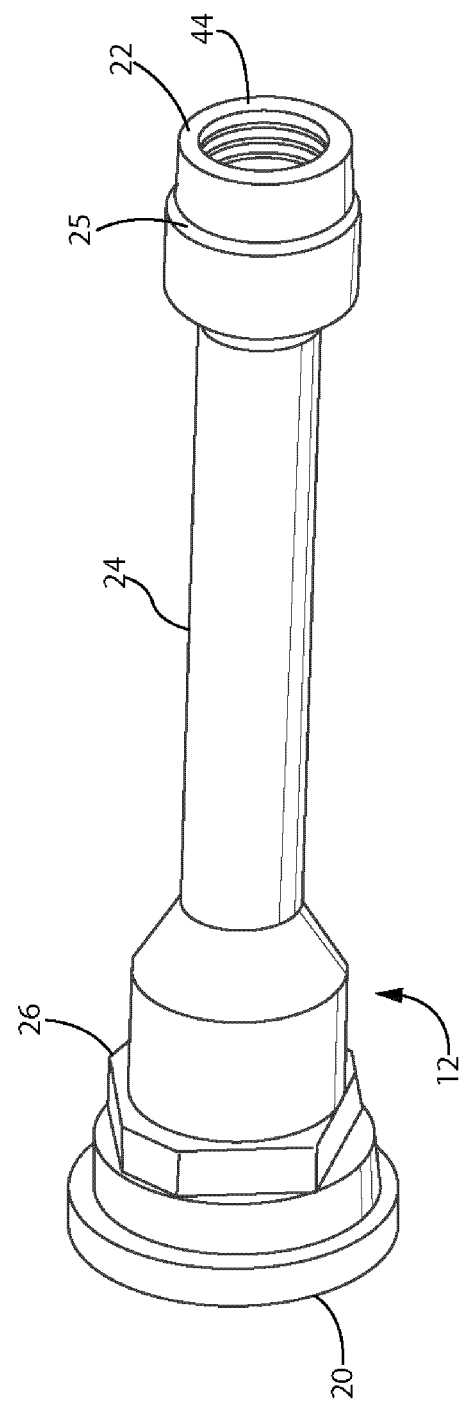
FIG. 9 is an isometric view of the core of the handle of FIG. 1.

Referring now in detail to the drawing figures, wherein like reference numerals represent like parts throughout the several views, one embodiment of a handle constructed according to the present disclosure is illustrated generally at 10 in FIG. 1. As best shown in FIGS. 1-4, this embodiment of the handle 10 is formed of a central core 12, a sleeve 14 disposed around the core 12, an outer skin 16 formed around the sleeve 14, and an end cap 18 engaged with one end of the core 12 and extending over the sleeve 14 and outer skin 16.

Referring now to FIGS. 1-4 and 9, the core 12 is shaped to accommodate a particular mechanism (not shown) therein, such as a ratcheting mechanism, a torque-limiting mechanism, or a variable gear ratio driving mechanism, among others, such as those disclosed in one or more of U.S. Pat. No. 6,817,458; U.S. Pat. No. 7,430,945; and/or U.S. Patent Application Publication No. US2010/0294084, which are each expressly incorporated by reference herein in their entirety. In the illustrated embodiment, the core 12 is formed with a generally tubular configuration with a wide first end 20 and a wide second end 22 joined by a narrow central passage 24. The first end 20 is shaped in a suitable machining process to accept any of a number of mechanisms therein to provide the desired utility for the handle 10. The first end 20 is configured to closely conform to the shape of the particular mechanism, and alternatively can be formed to be connectable to a number of different mechanisms in an interchangeable manner. A shaft (not shown) of a suitable implement can be inserted through the second end 22 along the passage 24 into engagement with mechanism disposed within the first end 20.

The second end 24 is also shaped in a suitable machining process to be able to accept any of a number of shaft securing mechanisms therein, in order to releasably secure the implement shaft within the core 12 in engagement with the mechanism disposed in the first end 22 of the handle 10.

The exterior of the first end 20 and the second end 22 are formed with engaging surfaces 25, 26, respectively, capable of contacting and engaging or mating with complementary surfaces 28 on the interior of the sleeve 14 to lock the core 12 in position with regard to the sleeve 14. In addition, both the first end 20 and the second end 22 extend beyond the ends of the sleeve 14 in order to facilitate the connection of the handle 10 to other components of the manufacture of the handle 10.

In the illustrated embodiment, the core 12 is formed as a single piece of a suitable material, such as stainless steel, that is capable of being sterilized effectively through the application of heated steam to the core 12, such as in an autoclave. In an alternative embodiment, the core 12 can be formed with the first end 20 and the second end 22 being separate from the passage 24, and the subsequently connected in any suitable manner to the respective ends of the passage 24, which in the illustrated embodiment has a diameter less than that of the first end 20 and the second end 22. In this embodiment, the first end 20 and second end 22 can be shaped to conform to a particular mechanism to be placed therein, further enhancing the ability of the core 12 to be adapted for particular uses of the handle 10. The core 12 has a diameter much less than the diameter of the sleeve 14 in order to greatly reduce the amount of material required for the formation of the core 12 and to provide a space 30 between the exterior of the core 12 and the interior of the sleeve 14 in the finished construction of the handle 10.

In either embodiment for the core 12, the configuration of the core 12 requires a minimum of separate machining steps, greatly reducing the amount of time required for the formation of the core 12.

Looking now at FIGS. 3-8, in the illustrated embodiment the sleeve 14 is formed as a hollow, generally tubular member having a front end 32 and a rear end 34. The front end 32 includes an inwardly tapering engagement ridge 36 and the rear end 34 includes a radially inwardly extending engagement flange 38. The engagement ridge 36 and the engagement flange 38 are shaped complementary to the engagement surfaces 25, 26 on the first end 20 and second end 22 of the core 12 in order to securely seat the core 12 within the sleeve 14.

The sleeve 14 is formed from a material that is heat resistant, meaning that the material can withstand the temperatures and/or pressures used to sterilize the handle 10. This material can be the same as that used for the core 12, or can be a different material. In certain embodiments, the sleeve 14 can be formed from a material such as metal, including aluminum, among others, or a plastic material.

When formed of these types of materials, especially plastic materials, the sleeve 14 can be formed by molding the material forming the sleeve 14 into the desired shape, which greatly reduces the amount of the material required and the time necessary to form the sleeve 14. Additionally, the sleeve 14 can be formed by hydroforming, stamping or in other similar processes, also resulting in significant reductions on used material and time for forming the sleeve 14. Also, because the sleeve 14 is formed according to one of these less intricate procedures, the sleeve 14 can be formed with more intricate shapes to enhance the desired attributes of the handle 10, as well as with a more uniform thickness along the length of the sleeve 14. This is especially true when the sleeve 14 is molded, as the mold can be designed with the particular form desired for the sleeve 14 to enable the sleeve 14 to be readily reproduced in a simple molding process. In addition, this more uniform thickness of the sleeve 14 along its length further speeds up the curing time for the sleeve 14, consequently speeding up the overall manufacturing process for the handle 10.

The outer skin 16 that is positioned on the exterior of the sleeve 14 is formed of any suitable material, such as a silicone material. The skin 16 is molded directly onto the sleeve 14 which is placed within the mold for the skin 16, with the material used to form the skin subsequently injected into the mold around the sleeve 14. Due to the shape of the sleeve 14 which, as a result of its construction and method of formation can be formed to more closely conform to the desired shape for the handle 10, the amount of material required to be injected around the sleeve 14 to form the skin 16 is greatly reduced. This consequently reduces the insulating ability of the skin 16 on the handle 10, thereby increasing the heat transfer along the handle 10. In one embodiment, the thickness of the material forming the skin 16 can be less than 15 mm, and in another embodiment can be less than 10 mm, and in still another embodiment can be less than 6 mm. The thickness of the skin 16 can also vary in one or both of the radial and axial directions of the handle 10 to provide the desired shape to the skin 16 and the handle 10, and in one embodiment the skin 16 can vary in thickness between about 0 mm and about 12 mm, and in another embodiment can vary between about 1 mm and about 8 mm, and in still another embodiment can vary between about 1 mm and about 5 mm.

To assist in holding the core 12 within the finished sleeve 14 and skin 16, once properly seated within the sleeve 14, the second end 22 of the core 12 is engaged with an inner member 40 of the end cap 18. The inner member 40 is formed to be generally tubular in shape and is positioned in alignment with the passage 24 in the core 12 to enable the shaft to pass through the inner member 40 of the cap 18 and the passage 24 of the core 12 for engagement with the mechanism disposed within the first end 20 of the core 12. In the illustrated embodiment, to hold the inner member 40 within the second end 22 of the core 12 the inner member 40 has a threaded outer surface 42 that is engaged with a complementary threaded surface 44 on the interior of the second end 22 of the sleeve 14, though other suitable engaging mechanism as are known in the art can be utilized as well.

The end cap 18 also includes an outer member 46 that functions to engage the exterior of the skin 16 and sleeve 14 and hold the core 12 within the sleeve 14. In the illustrated embodiment, the outer member 46 is conical in shape and extends axially outwardly from the inner member 40 in a direction that partially overlaps the inner member 40. When the inner member 40 is engaged with the core 12, an engagement surface 48 on the outer member 46 engages and compresses the skin 16 against the sleeve 14 while simultaneously drawing the second end 22 of the core 12 into secure and aligned engagement with the sleeve 14. The end cap 18 can be formed from any suitable material, but in the illustrated embodiment is formed from a metal, such as stainless steel.

When fully assembled, the insulating effect of the skin 16 on the core 12 is consequently reduced as a result of the presence of the space 30 defined between the core 12 and the sleeve 14/skin 16 and the more consistent thickness of the skin 16 disposed on the exterior of the sleeve 14. As a result, when the handle 10 is disposed in an autoclave for the purposes of sterilizing the handle 10, the steam can more quickly raise the temperature of the core 12 to enable the handle 10 to be effectively heated and sterilized within the predetermined treatment cycles of the autoclave, even a high speed autoclave. Further, with the construction of the handle 10, the particular mechanism disposed within the core 12 can be removed from the care 12 to enable the core 12 to be more effectively sterilized.

In other alternative embodiments, the end cap 18 can be omitted or formed as a component of the core 12, or the sleeve 14 and skin 16 can be formed as a single member, such that only one molding step is required to for the sleeve 14 or skin 16 to be secured around the core 12.

In still other alternative embodiments, the space 30 between the exterior of the core 12 and the interior of the sleeve 14 can be utilized to house any of a number of different devices or mechanisms to enhance the utility of the handle 10, such as any of a number of electronic devices, among others.

Various other embodiments of the present disclosure are contemplated as being within the scope of the filed claims particularly pointing out and distinctly claiming the subject matter regarded as the invention.

We claim:

1. A modular handle comprising:
   a) a hollow core including a first end and a second end joined by a passage, the core including a tool mechanism disposed therein;
   b) a sleeve formed at least partially of a rigid, moldable and temperature resistant material and releasably secured around the core to define a space between the core and the sleeve; and
   c) an outer skin positioned on the sleeve opposite the core.

2. The modular handle of claim 1 wherein the outer skin is formed of a moldable insulating material.

3. The modular handle of claim 2 where in the range of thickness for the outer skin is between about 0 mm and about 15 mm.

4. The modular handle of claim 3 wherein the range of thickness for the outer skin is between about 1imn and about 8 mm.

5. The modular handle of claim 1 wherein the core includes at least one engagement surface mateable with the sleeve to retain the core in position within the sleeve.

6. The modular handle of claim 5 wherein the sleeve includes at least one engagement ridge shaped complementary to and engageable with the at least one engagement surface.

7. The modular handle of claim 5 wherein the sleeve includes at least one engagement flange shaped complementary to and engageable with the at least one engagement surface.

8. The modular handle of claim 1 further comprising an end cap engaged with the second end of the core and the sleeve.

9. The modular handle of claim 8 wherein the end cap is frictionally engaged with the sleeve and threadably engaged with the second end of the core.

10. The modular handle of claim 1 wherein the tool mechanism disposed in the first end of the core.

11. The modular handle of claim 10 further comprising a shaft of an implement inserted through the second end of the core and engaged with the tool mechanism within the first end of the core.

12. The modular handle of claim 1 wherein the first end of the core has a diameter larger than a diameter of a tubular section connecting the first end and the second end.

* * * * *